(12) United States Patent
Piferi et al.

(10) Patent No.: US 7,602,190 B2
(45) Date of Patent: Oct. 13, 2009

(54) EXTERNAL MRI IMAGING COIL ASSEMBLIES AND MRI-GUIDED INTERVENTIONAL SYSTEMS UTILIZING SAME

(75) Inventors: Peter Piferi, Orange, CA (US); Christopher Keidl, Hartland, WI (US); David Peterson, Archer, FL (US)

(73) Assignee: SurgiVision, Inc., Memphis, TN (US)

( * ) Notice: Subject to any disclaimer, the term of this patent is extended or adjusted under 35 U.S.C. 154(b) by 0 days.

(21) Appl. No.: 12/237,102

(22) Filed: Sep. 24, 2008

(65) Prior Publication Data

US 2009/0079431 A1    Mar. 26, 2009

Related U.S. Application Data

(60) Provisional application No. 60/974,821, filed on Sep. 24, 2007.

(51) Int. Cl.
*G01V 3/00* (2006.01)
(52) U.S. Cl. .......... 324/318; 324/322; 600/422
(58) Field of Classification Search .......... 600/422; 324/318, 322
See application file for complete search history.

(56) References Cited

U.S. PATENT DOCUMENTS

| | | | |
|---|---|---|---|
| 5,085,219 A * | 2/1992 | Ortendahl et al. ........... 600/422 |
| 6,177,797 B1 | 1/2001 | Srinivasan |
| 6,198,961 B1 * | 3/2001 | Stern et al. ................. 600/422 |
| 6,198,962 B1 * | 3/2001 | Su ............................. 600/422 |
| 6,577,888 B1 | 6/2003 | Chan et al. |
| 6,591,128 B1 * | 7/2003 | Wu et al. ..................... 600/422 |
| 2002/0049451 A1 | 4/2002 | Parmer et al. |
| 2002/0052610 A1 | 5/2002 | Skakoon et al. |
| 2002/0190716 A1 | 12/2002 | Misic |
| 2004/0215279 A1 | 10/2004 | Houben et al. |
| 2004/0228796 A1 | 11/2004 | Talpade |

FOREIGN PATENT DOCUMENTS

| | | |
|---|---|---|
| DE | 10029736 A1 | 1/2002 |
| DE | 102005062716 A1 | 7/2007 |
| WO | WO 97/35206 | 9/1997 |
| WO | WO 98/52064 A | 11/1998 |
| WO | WO 02/39135 A2 | 5/2002 |
| WO | WO 03/102614 A | 12/2003 |

OTHER PUBLICATIONS

Notification of Transmittal of the International Search Report and the Written Opinion of the International Searching Authority for corresponding PCT Application Serial No. PCT/US2008/011073 issued by the European Patent Office on Feb. 18, 2009.

* cited by examiner

*Primary Examiner*—Louis M Arana
(74) *Attorney, Agent, or Firm*—Myers Bigel Sibley & Sajovec, P.A.

(57) ABSTRACT

An MRI imaging coil assembly includes a primary external MRI imaging coil and a secondary external MRI imaging coil positioned proximate to the primary MRI imaging coil. The primary imaging coil has a plurality of spaced-apart RF coils and is configured to surround at least a portion of a patient. The secondary imaging coil has at least one RF coil and cooperates with the primary imaging coil to provide MRI signals to an MRI scanner. The secondary imaging coil can be movably positioned relative to the primary imaging coil. The secondary imaging coil can be movably secured to the primary imaging coil or to a patient support surface.

25 Claims, 12 Drawing Sheets

EXTERNAL MRI IMAGING COIL ASSEMBLIES AND MRI-GUIDED INTERVENTIONAL SYSTEMS UTILIZING SAME

RELATED APPLICATIONS

This application claims the benefit of and priority to U.S. Provisional Patent Application No. 60/974,821, filed Sep. 24, 2007, and U.S. patent application Ser. No. 12/134,412, filed Jun. 6, 2008, the disclosures of which are incorporated herein by reference as if set forth in their entireties.

FIELD OF THE INVENTION

The present invention relates generally to medical systems and apparatus and, more particularly, to MRI-interventional systems and apparatus.

BACKGROUND

Deep Brain Stimulation (DBS) is becoming an acceptable therapeutic modality in neurosurgical treatment of patients suffering from chronic pain, Parkinson's disease or seizure, and other medical conditions. Other is electro-stimulation therapies have also been carried out or proposed using internal stimulation of the sympathetic nerve chain and/or spinal cord, etc. One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum.

Real-time MRI-guided tools and procedures for DBS, as well as for other interventional medical procedures, are being developed. However, the quality of an MRI image depends on the strength of the received signal. As such radio frequency (RE) receiving coils typically are placed in close proximity to the area of a patient being imaged. These coils are often referred to as surface or is head coils. One type of head coil used for imaging of the brain is a "bird cage" coil, as described in U.S. Pat. No. 6,396,271. Typically, a birdcage coil has a pair of circular end rings which are bridged by a plurality of equally-spaced straight segments or legs about the periphery of a cylindrical volume. A patients head fits through one of the end rings and into the enclosed volume and a patient is typically unrestrained and able to move.

SUMMARY

In view of the above, improved MRI imaging coil assemblies for use during MRI-guided procedures are provided. According to some embodiments of the present invention, an MRI imaging coil assembly includes a primary external imaging coil and a secondary external imaging coil positioned proximate to the primary imaging coil. The primary imaging coil has a plurality of spaced-apart RE coils and is configured to surround at least a portion of a patient (e.g., a patient's head). The secondary imaging coil has at least one RF coil and cooperates with the primary imaging coil to provide MRI signals to an MRI scanner. The primary imaging coil provides MRI signals to an MRI scanner of a target region of a patient's body, and the secondary imaging coil provides MRI signals to an MRI scanner of an interventional device being utilized during an MRI-guided procedure.

In some embodiments, the primary imaging coil completely surrounds a portion of a patient. In some embodiments, the primary imaging coil has an open-face, substantially U-shaped configuration that does not completely surround a portion of a patient. In some embodiments, the secondary imaging coil can have a planar configuration; in other embodiments, the secondary imaging coil can have an arcuate configuration.

In some embodiments, a primary imaging coil extends longitudinally to define a first direction and a secondary imaging coil is movably positioned proximate to the primary imaging coil along the first direction and/or along a second direction transverse to the first direction. In some embodiments, the secondary imaging coil is movably secured to the primary imaging coil. In some embodiments, the secondary imaging coil is movably secured directly to a patient support surface, such as a gantry associated with an MRI scanner, or other object adjacent to the primary imaging coil. In some embodiments, the primary and secondary imaging coils are telescopically adjustable relative to each other.

In some embodiments, two or more secondary imaging coils may be positioned proximate to a primary imaging coil. The secondary imaging coils may be in adjacent, spaced-apart relationship, and may be movably secured to the primary imaging coil or movably secured to a patient support surface, or other object, adjacent to the primary imaging coil.

According to some embodiments of the present invention, an MRI-guided interventional system includes a patient support surface (e.g., a gantry associated with an MRI scanner), a head support assembly attached to the patient support surface for immobilizing the head of a patient during an MRI-guided procedure, a targeting frame configured to be secured to the skull of a patient, and an MRI imaging coil assembly. The targeting frame includes a cooperating targeting cannula that is configured to guide placement of an interventional device through a burr hole in the skull of the patient in vivo. The imaging coil assembly includes a primary external imaging coil and a secondary external imaging coil positioned proximate to the primary imaging coil. The primary imaging coil has a plurality of spaced-apart RF coils and is configured to surround at least a portion of a patient's head. The secondary imaging coil has at least one RF coil and cooperates with the primary imaging coil to provide MRI signals to an MRI scanner. The primary imaging coil provides MRI signals to an MRI scanner of a target region of a patient's body (i.e., the brain, etc.), and the secondary imaging coil provides MRI signals to an MRI scanner of the targeting frame/targeting cannula. The primary imaging coil extends longitudinally to define a first direction, and the secondary imaging coil is movably positioned proximate to the primary MRI imaging coil along the first direction and/or along a second direction transverse to the first direction.

MRI imaging coil assemblies according to embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, MRI-guided ablation procedures, etc.

MRI imaging coil assemblies according to embodiments of the present invention can be advantageous over conventional systems because they can be easily adjustable for various patient head sizes and shapes. MRI imaging coil assemblies, according to embodiments of the present invention can be sterilized within an autoclave, and can be wiped down with disinfectant and cleaners. In addition, imaging coil assemblies, according to embodiments of the present invention can be installed and used many times without degradation, or may be single-use and disposable.

DETAILED DESCRIPTION

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "MRI compatible" means that a device is safe for use in an MRI environment and/or can operate as intended in an MRI environment, and, as such, if residing within the high-field strength region of the magnetic field, is typically made of a non-ferromagnetic MRI compatible material(s) suitable to reside and/or operate in a high magnetic field environment.

The term "gantry" refers to a patient support of an MRI scanner and may include the patient table or other structure.

The term "rod" refers to an elongate member with rigidity, such as a bolt, pin, screw, etc. For example, a head engagement rod is an elongate member with sufficient structural rigidity to secure the head of a patient.

MRI imaging coil assemblies according to embodiments of the present invention facilitate guiding and/or placing diagnostic or interventional devices and/or therapies to any desired internal region of the brain. For example, imaging coil assemblies according to embodiments of the present invention facilitate the placement of implantable DBS leads for brain stimulation, typically deep brain stimulation, and facilitate delivering tools or therapies that stimulate a desired region of the sympathetic nerve chain. Embodiments of the present invention can be used with any MRI scanner system, including open and closed bore designs and any field strength, typically 1.0 T-10 T.

Embodiments of the present invention have other uses inside or outside the brain include stem cell placement, gene therapy or drug delivery for treating physiological conditions. Some embodiments can be used to treat tumors. Some embodiments can be used for diagnosing or delivering any desired therapy such as, for example, RF stimulation or ablation, laser stimulation or ablation, cryogenic stimulation or ablation, etc.

Figure 1:
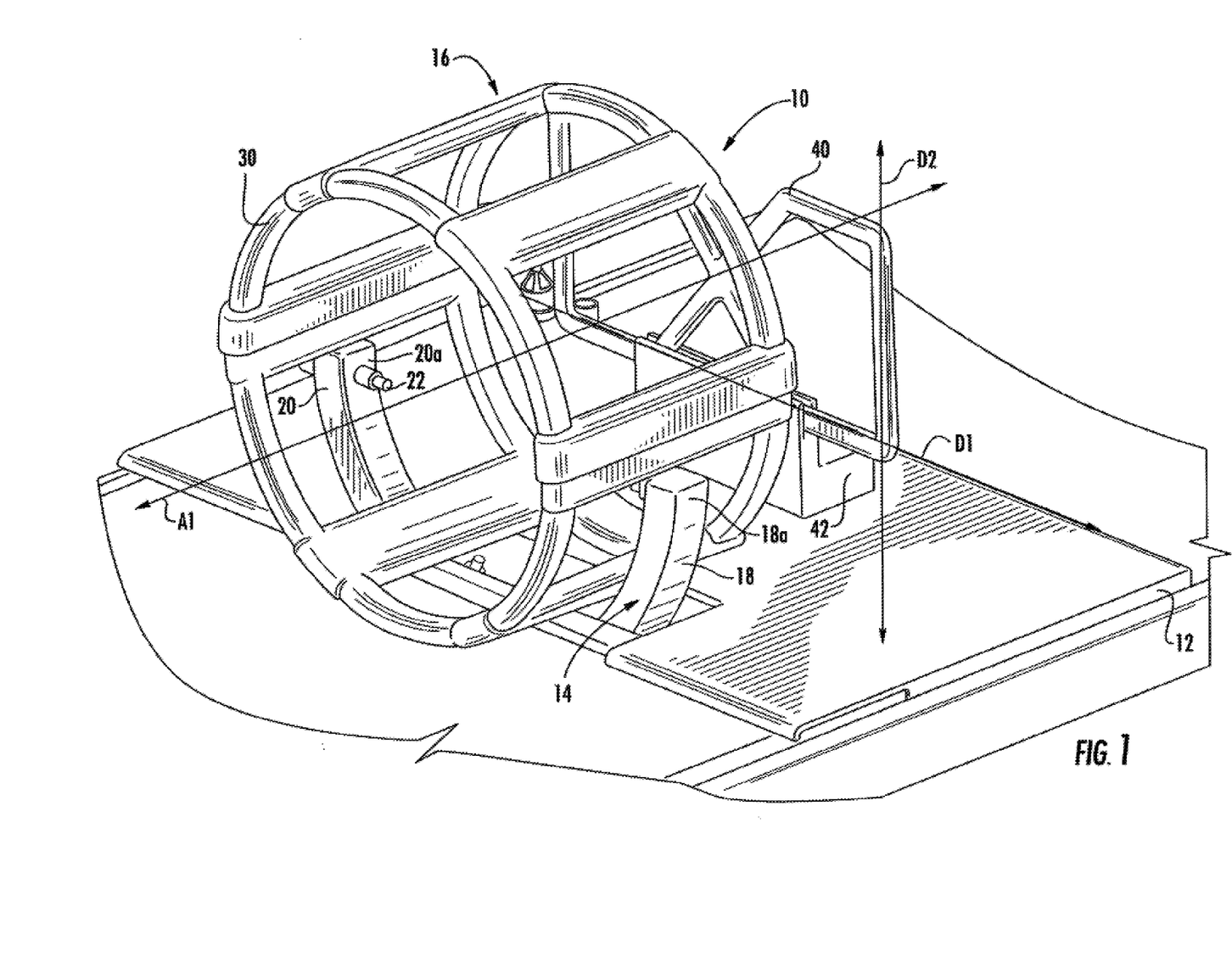
FIGS. 1-2 are perspective views of an MRI imaging coil assembly, according to some embodiments of the present invention.

Embodiments of the present invention will now be described in detail below with reference to the figures. Referring initially to FIG. 1, an MRI-guided interventional system 10, according to some embodiments of the present invention, is illustrated. A patient support surface 12, such as a gantry associated with an MRI scanner, has a head support assembly 14 and an MRI imaging coil assembly 16 associated therewith. The head support assembly 14 is configured to immobilize the head of a patient during an MRI-guided procedure, and includes a pair of elongated arms 18, 20 that extend upwardly from the patient support surface 12 in adjacent, spaced-apart relationship to form a space for receiving the head of a patient. The illustrated arms 18, 20 lie in substantially the same plane (i.e., are substantially co-planar) and have an arcuate configuration. Each arm 18, 20 of the head support assembly 14 includes a respective free end 18a, 20a. A head engagement rod 22 is adjustably associated near each respective arm free end 18a, 20a. The head engagement rods 22 are configured to engage a patient's head within the head support assembly 14.

Embodiments of the present invention are not limited to the illustrated head support assembly 14. Head support assemblies utilized in conjunction with embodiments of the present invention can have various structural configurations, without limitation. For example, exemplary head support assemblies that can be utilized with embodiments of the present invention are described in copending U.S. patent application Ser. No. 12/237,091, filed Sep. 24, 2008, which is incorporated herein by reference in its entirety.

Associated with the head support assembly 14 is an MRI imaging coil assembly 16 that includes a primary external imaging coil 30 and a secondary external imaging coil 40 positioned proximate to the primary imaging coil 30. The primary and secondary imaging coils 30, 40 cooperate to provide MRI signals to an MRI scanner. The primary imaging coil 30 is configured to provide MRI signals to an MRI scanner of a target region of a patient's body, such as the brain. The secondary imaging coil 40 provides MRI signals to an MRI scanner of an interventional device being utilized during an MRI-guided procedure. In some embodiments, an image produced by the MRI imaging coil assembly 16 has no greater than one-hundred percent (100%) difference in signal-to-noise ratio (SNR) across a volume thereof.

Figure 2:
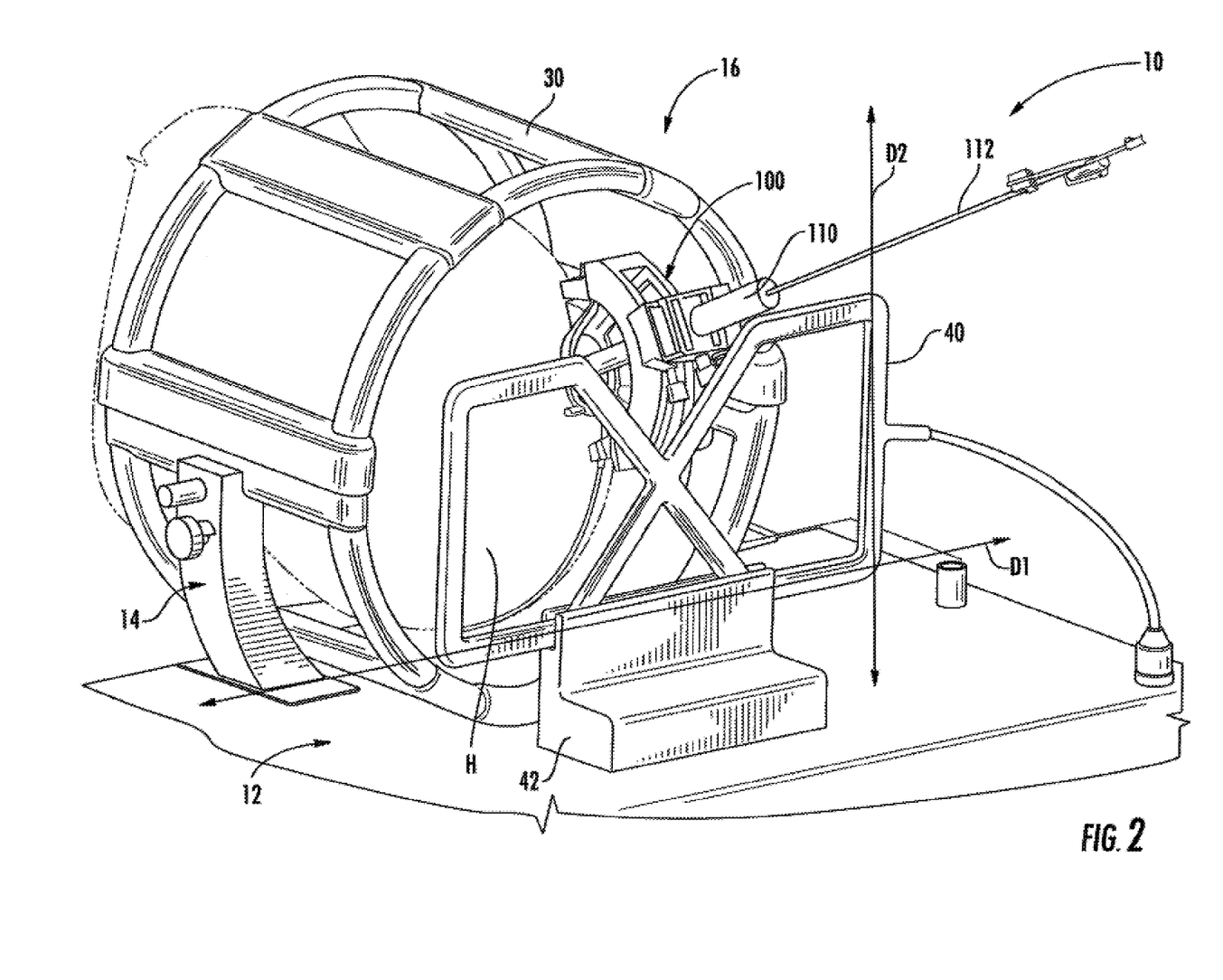
Figure 10:
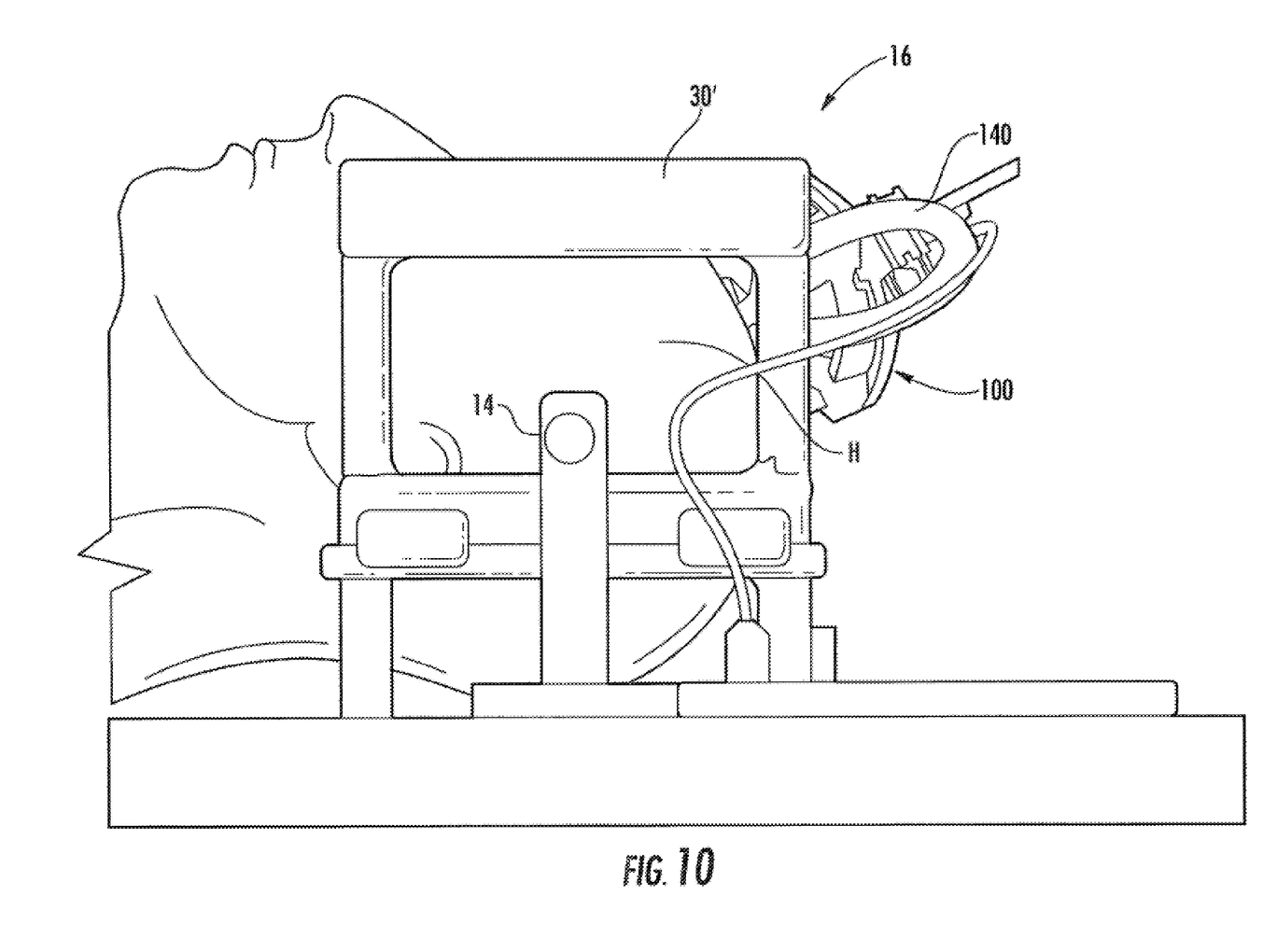
FIG. 10 is a side view of an MRI imaging coil assembly, according to some embodiments of the present invention.

As shown in FIGS. 2 and 10, the primary imaging coil 30 can be secured to the head support assembly 14 and is configured to surround at least a portion of the head H of a patient. However, embodiments of the present invention do not require the primary imaging coil 30 to be secured to the head support assembly 14. The primary imaging coil 30 can be supported/secured in various ways and to other portions of an MRI scanner apparatus (e.g., to the gantry, to a base attached to the gantry etc.)

The primary imaging coil 30 has a plurality of spaced-apart RF coils, along with circuitry associated therewith. The RF coils within the primary head coil 30 can be positioned as desired relative to a patient's head. An exemplary supplier of RF coils that may be utilized is Midwest RF, LLC., Hartland, Wis. Embodiments of the present invention are not limited to the illustrated configuration of the primary imaging coil 30. Other configurations, such as illustrated in FIGS. 5-9 and 11, may be utilized. In each of the illustrated embodiments, the RF coils within the primary imaging coils can be positioned as desired relative to a patient's head.

The secondary imaging coil 40 is positioned at one end of the primary imaging coil 30, as illustrated in the figures, and has at least one RF coil. The secondary imaging coil 40 is secured to the patient support surface 12 via mount 42. The secondary imaging coil 40 illustrated in FIGS. 1-2 has a substantially planar configuration and is oriented such that a plane defined thereby is substantially transverse to longitudinal axis $A_1$ defined by the primary imaging coil 30.

The secondary imaging coil mount 42 allows the secondary imaging coil 40 to be positioned proximate to the primary imaging coil 30 along the axis $A_1$ and along directions $D_1$ and $D_2$. For example, the secondary imaging coil 40 may be movable within the mount 42 (or the mount 42 may be movable) along direction $D_1$. The secondary imaging coil 40 may be raised and lowered within the mount 42 (or the mount 42 may be raised and lowered) along direction $D_2$. In addition, mount 42 may be movably positioned proximate to the primary imaging coil 30 along axis $A_1$.

FIG. 2 illustrates the MRI-guided interventional system 10 of FIG. 1 with a patient's head H secured within the head support assembly 14 and with a trajectory or targeting frame 100 secured to the skull of the patient. The targeting frame 100 supports a cooperating targeting cannula 110 that is configured to guide placement of an interventional device through a burr hole in the skull of the patient in vivo. The frame 100 is adjustable such that the targeting cannula 110 is rotatable about a pitch axis, about a roll axis, and such that the targeting cannula can translate in X-Y directions. An exemplary targeting frame is described in U.S. patent application Ser. No. 12/134,412, filed Jun. 6, 2008, which is incorporated herein by reference in its entirety.

In the illustrated embodiment of FIG. 2, the secondary MRI imaging coil 40 may be focused to the targeting frame 100, to the targeting cannula 110, and/or to an interventional device 112 extending through the targeting cannula 110 and into the patient. In addition or alternatively, the secondary MRI imaging coil 40 may be focused on a subset of a volume of intrabody region of a patient (e.g., a patient's STN or other target deep brain region).

Figure 3:
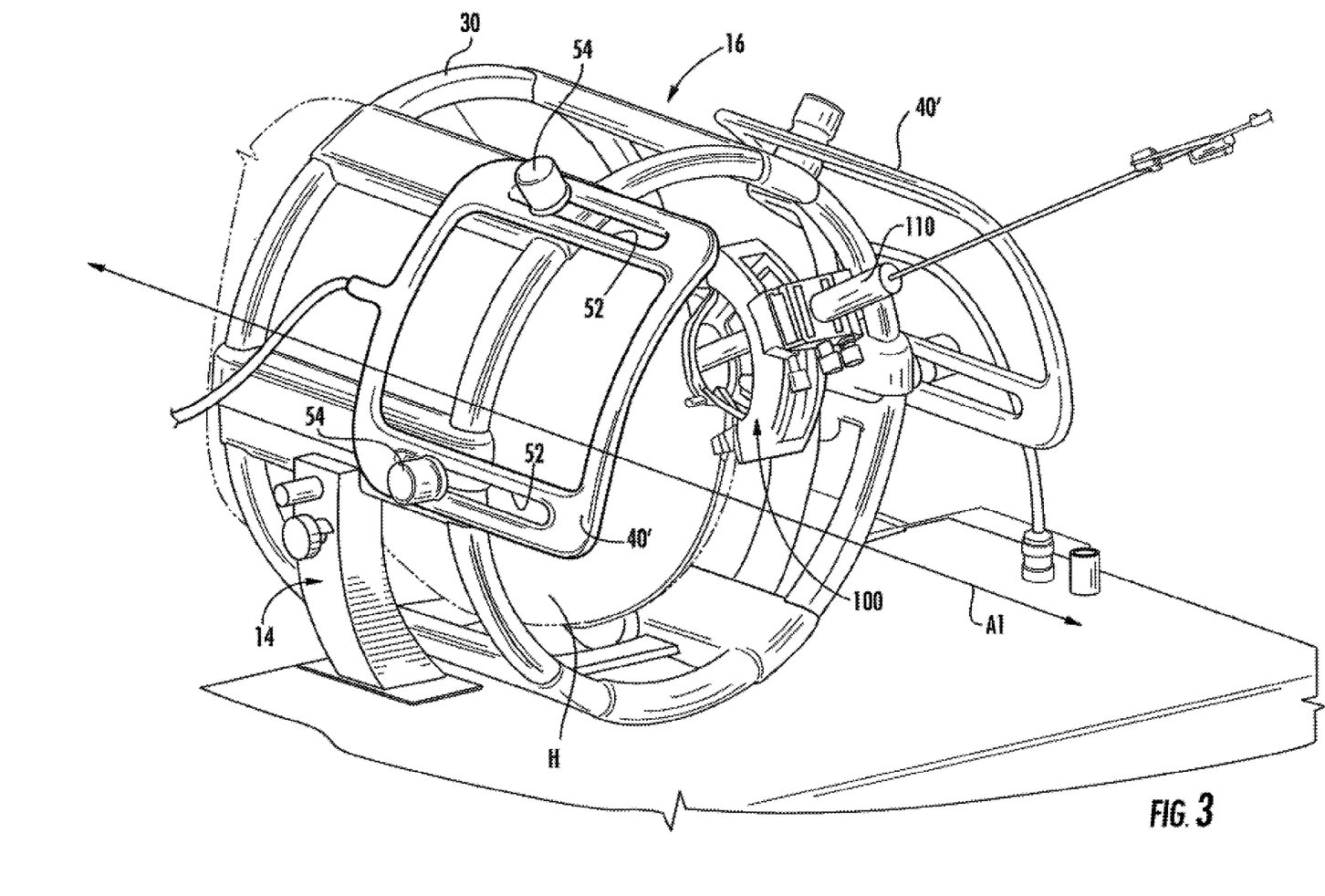
FIG. 3 is a perspective view of an MRI imaging coil assembly, according to some embodiments of the present invention.

FIG. 3 illustrates an MRI imaging coil assembly 16 according to another embodiment of the present invention. The illustrated MRI imaging coil assembly 16 includes a primary external MRI imaging coil 30 and a pair of secondary external MRI imaging coils 40' positioned proximate to the primary MRI imaging coil 30. The secondary imaging coils 40' are movably secured to the primary imaging coil 30 in adjacent, spaced-apart relationship, as illustrated. The secondary imaging coils 40' can have an arcuate shape and are configured to slide telescopically along the outer periphery of the primary imaging coil 30. Each secondary imaging coil 40' includes a pair of spaced-apart slots 52 that engage respective locking members 54. Locking members 54 can be loosened to permit the secondary imaging coils 40' to move along the axial direction $A_1$ and can be tightened to secure the secondary imaging coils 40' in a desired location.

Figure 4:
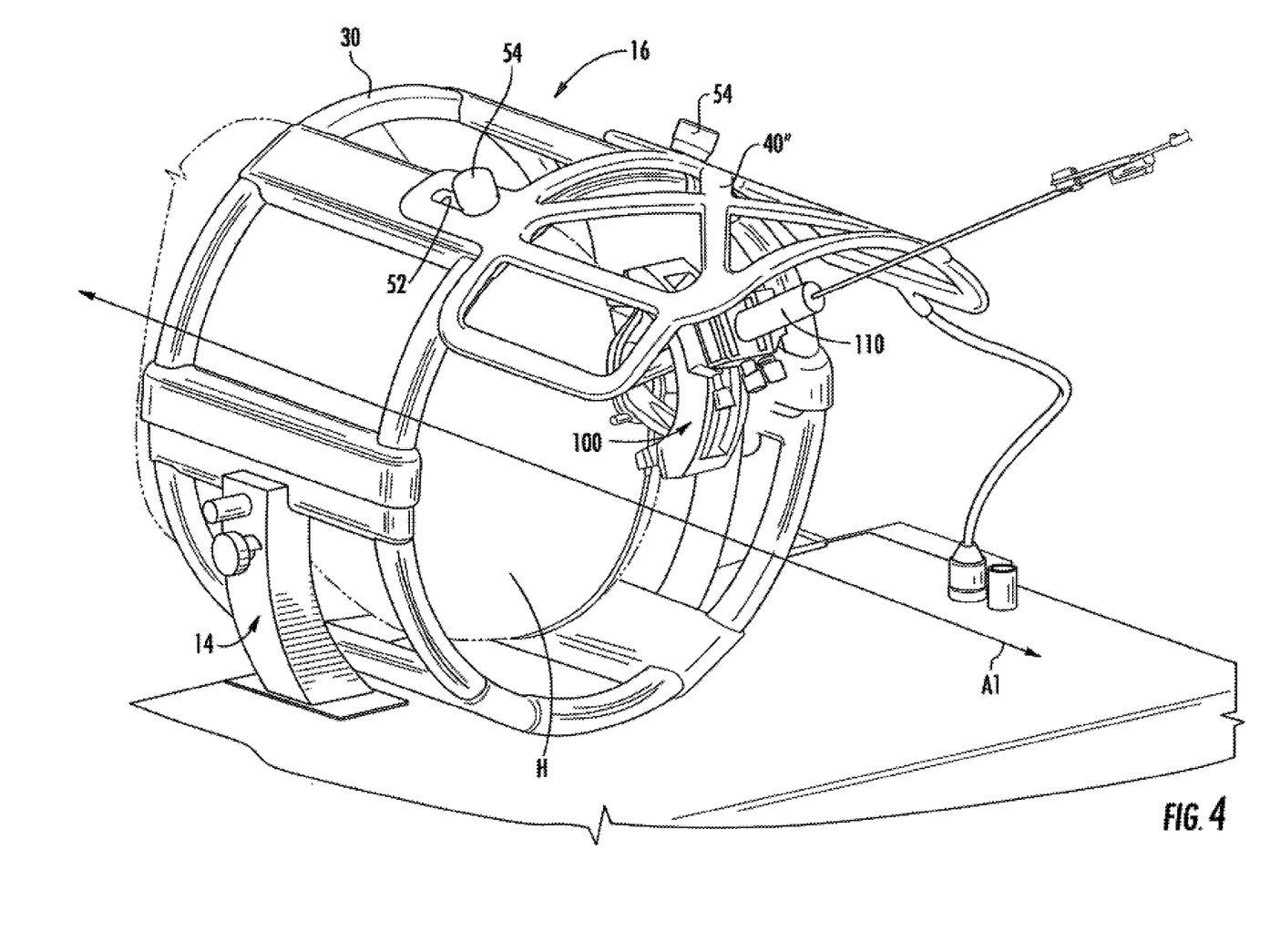
FIG. 4 is a perspective view of an MRI imaging coil assembly, according to some embodiments of the present invention.

FIG. 4 illustrates an MRI imaging coil assembly 16 according to another embodiment of the present invention. The illustrated MRI imaging coil assembly 16 includes a primary external MRI imaging coil 30 and a secondary external MRI imaging coil 40" positioned proximate to the primary MRI imaging coil 30. The secondary imaging coil 40" is movably secured to the primary imaging coil 30, as illustrated. The secondary imaging coil 40" has an arcuate shape and is configured to slide telescopically along the outer periphery of the primary imaging coil 30. The secondary imaging coil 40" includes a pair of spaced-apart slots 52 that engage respective locking members 54. Locking members 54 can be loosened to permit the secondary imaging coil 40" to move along the axial direction $A_1$ and can be tightened to secure the secondary imaging coil 40" in a desired location.

Figure 5:
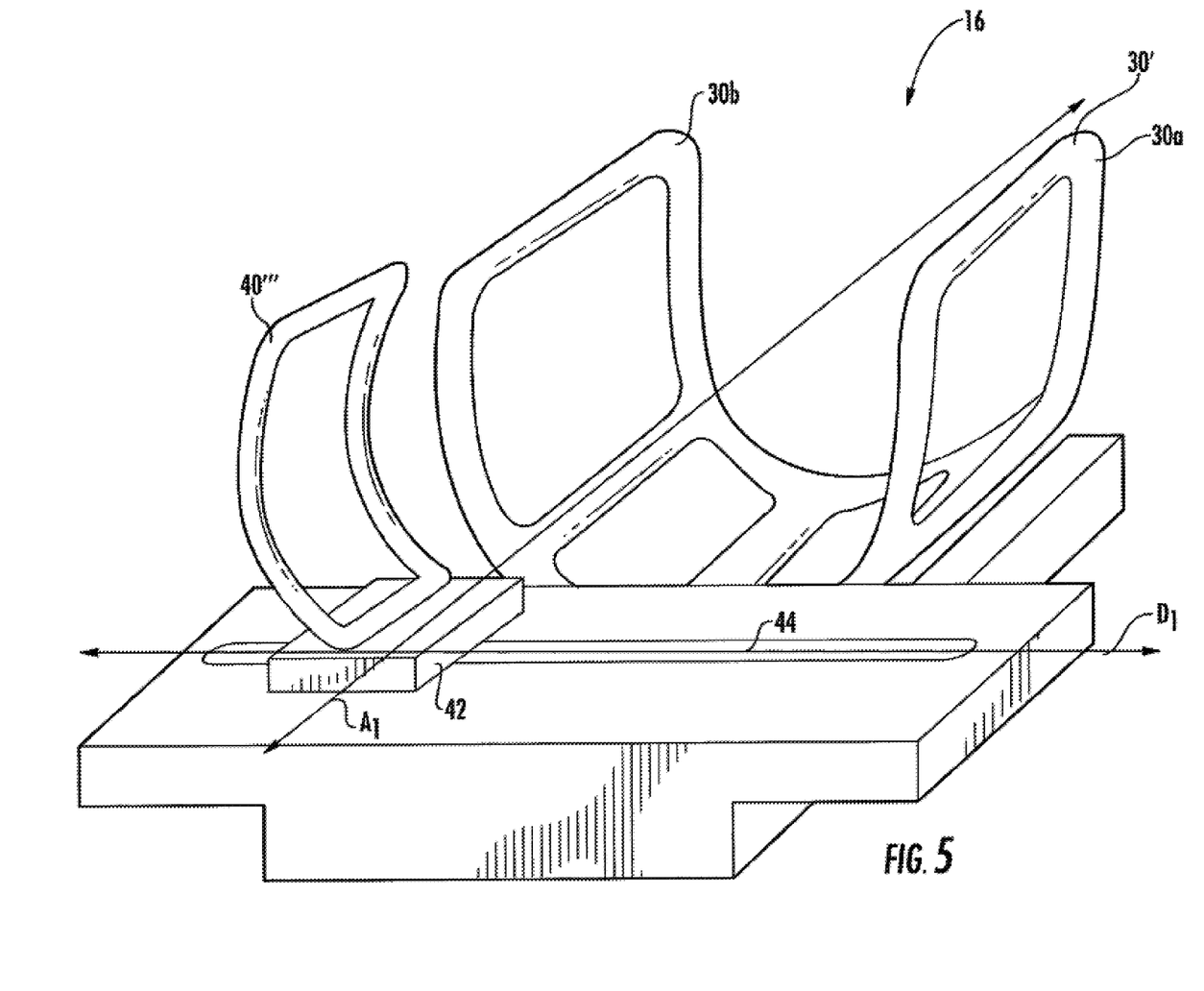
FIG. 5 is a perspective view of an MRI imaging coil assembly, according to some embodiments of the present invention.

FIG. 5 illustrates an MRI imaging coil assembly 16 according to another embodiment of the present invention. The illustrated MRI imaging coil assembly 16 includes a primary external MRI imaging coil 30' and a secondary external MRI imaging coil 40'" positioned proximate to the primary MRI imaging coil 30'. The secondary imaging coil 40'" is movably secured to the patient support surface 12 via a mount 42', as illustrated. The secondary imaging coil 40'" can have an arcuate shape and is configured to move along a direction $D_1$ that is transverse to an axial direction $A_1$ defined by the primary imaging coil 40'. The patient support surface 12 includes a slot 44 within which mount 42' slidably engages.

The primary imaging coil 30' has an open-face, substantially U-shaped configuration with spaced-apart leg portions 30a, 30b having free ends. The primary imaging coil 30' is configured to be secured to the patient support surface 12, or to a base attached to the patient support surface 12, between the head support arms of a head support assembly (e.g., arms 18, 20 of head support assembly 14 illustrated in FIGS. 1-4) such that the free ends of the leg portions 30a, 30b extend upwardly.

Figure 6:
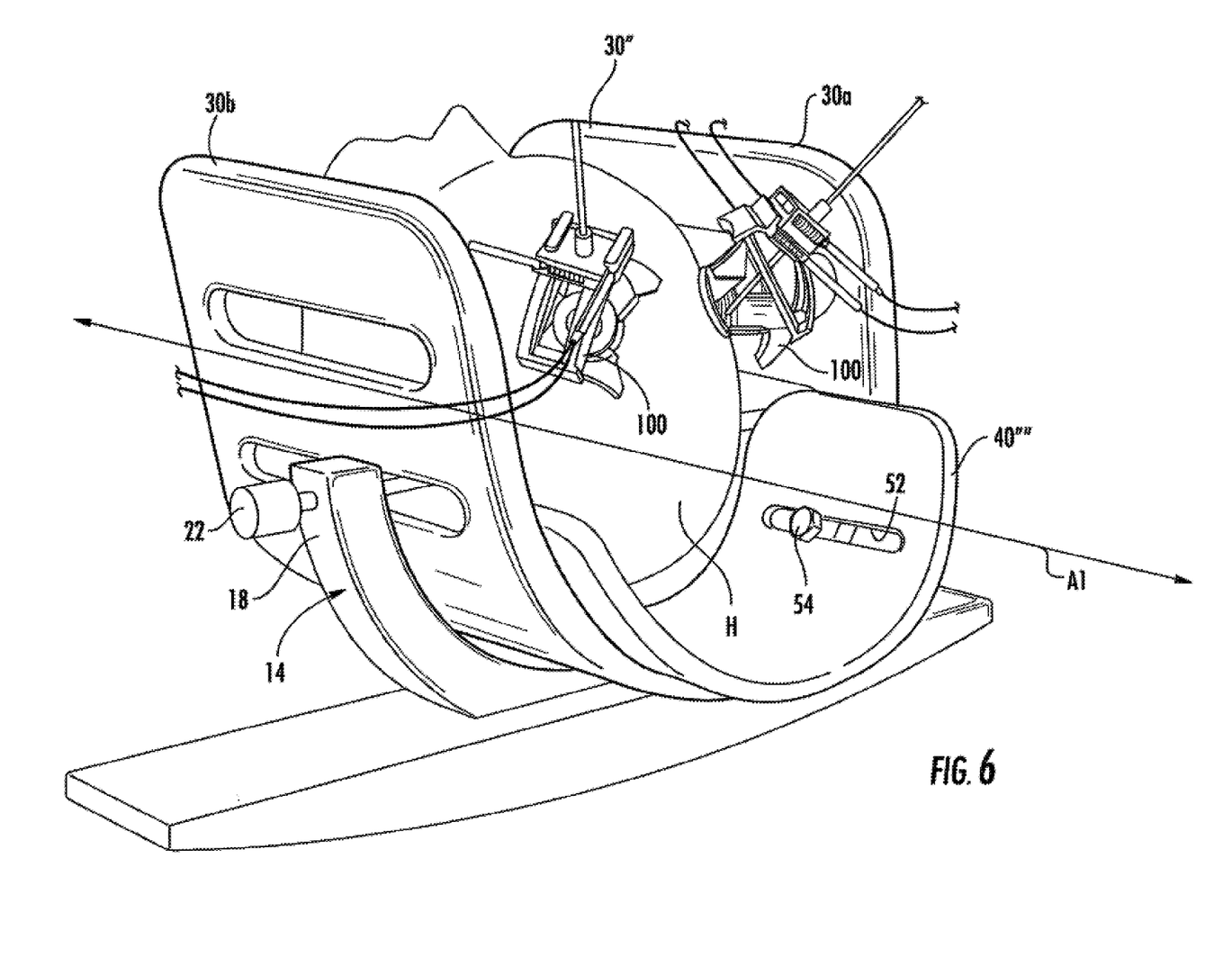
FIG. 6 is a perspective view of an MRI imaging coil assembly, according to some embodiments of the present invention.
Figure 7:
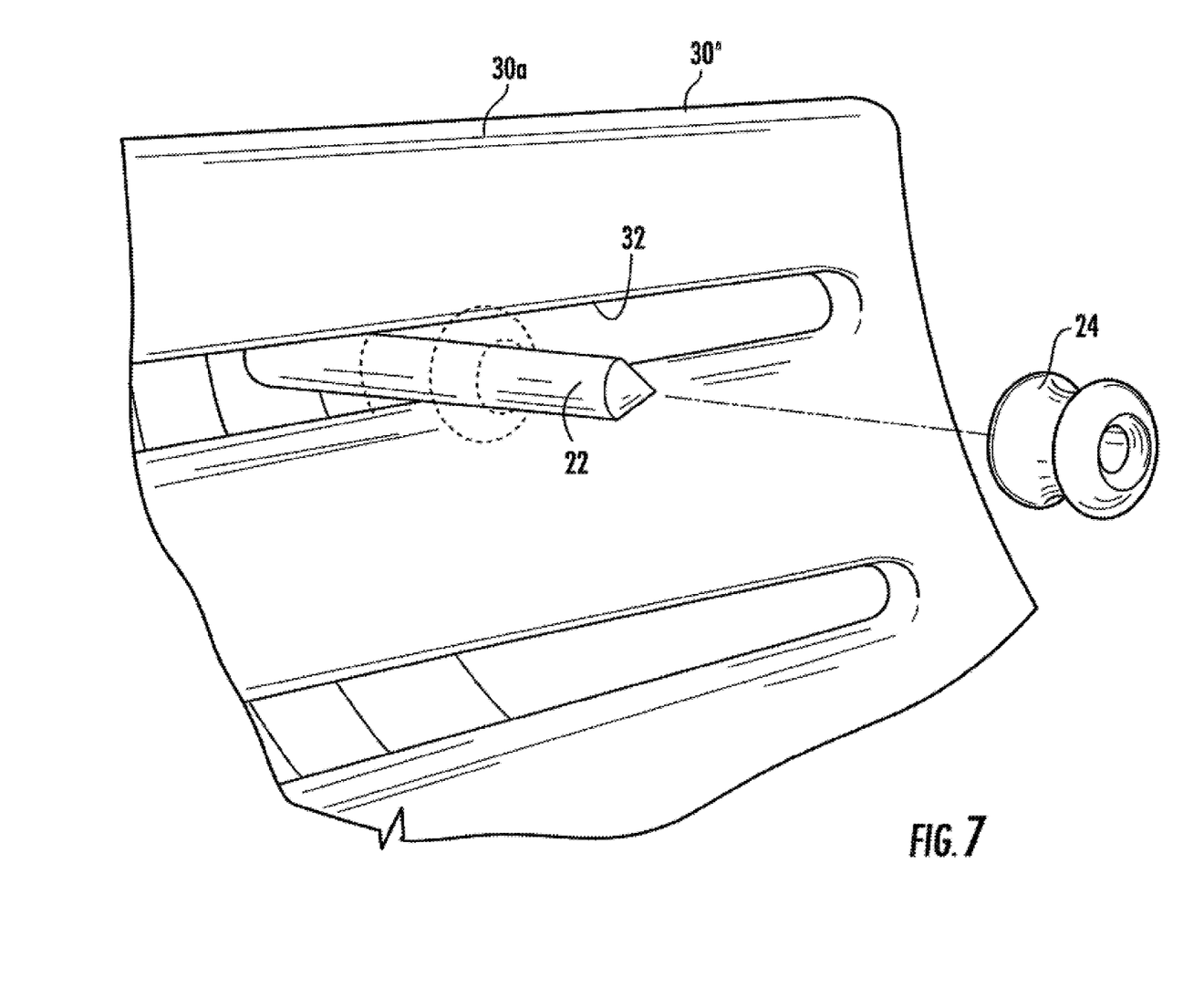
FIG. 7 is an partial exploded view of the MRI imaging coil assembly of FIG. 6, illustrating the mounting configuration of the primary imaging coil thereof to a head support assembly.
Figure 8:
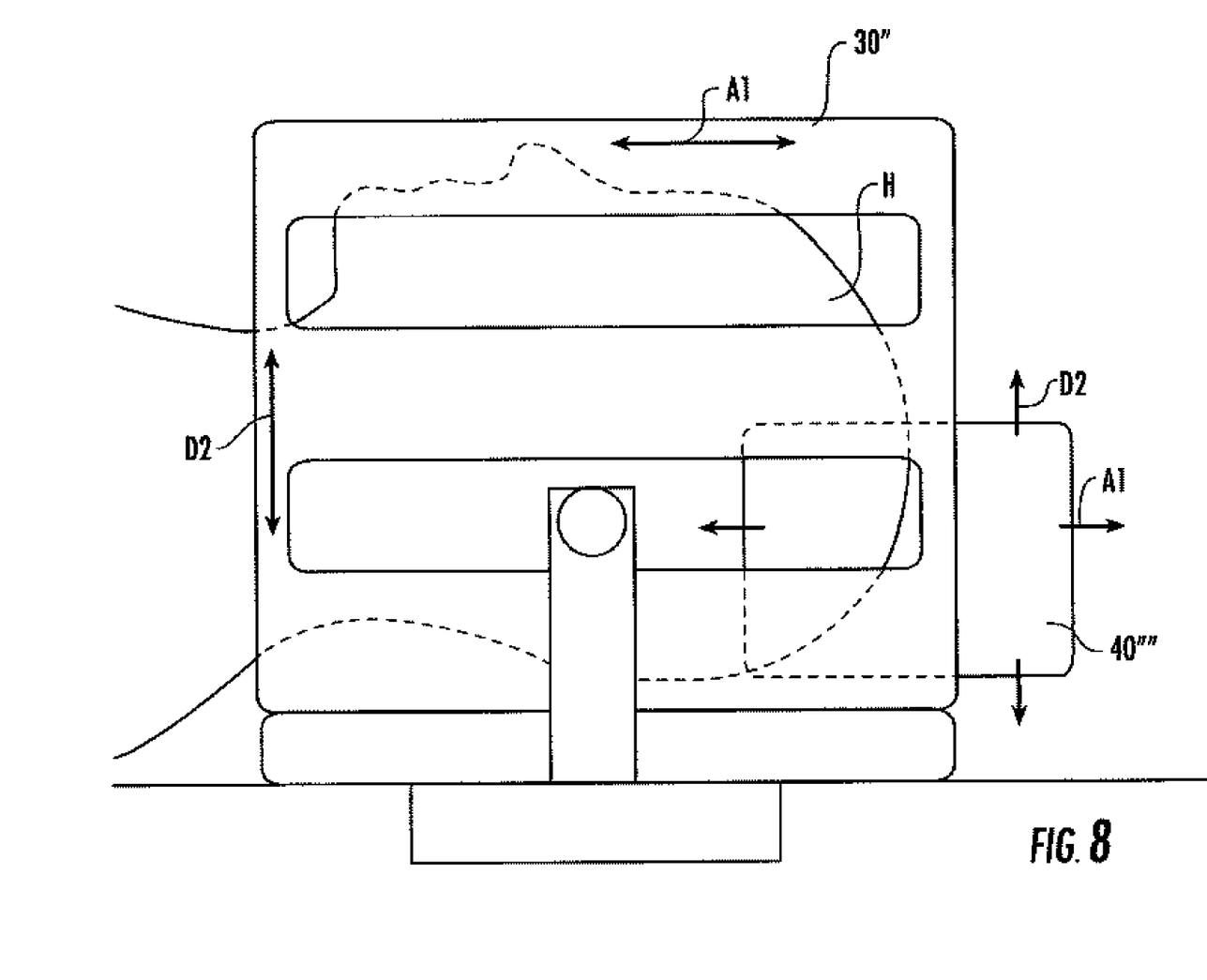
FIG. 8 is a schematic illustration of movement directions for the primary and secondary imaging coils of the imaging coil assembly of FIG. 6.
Figure 9A:
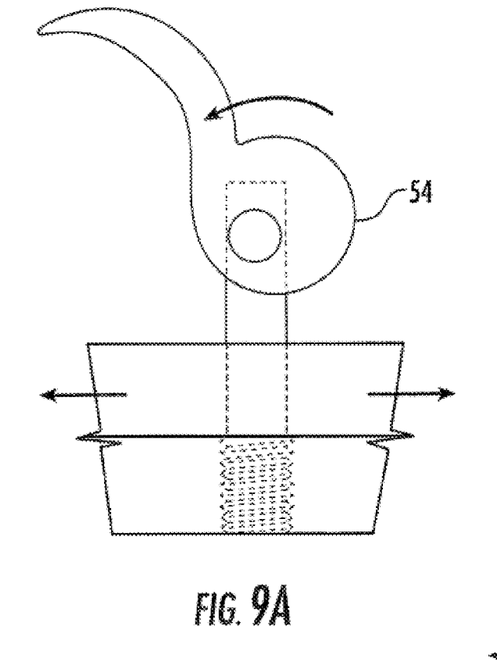
FIGS. 9A-9C illustrate exemplary types of locking members for securing the secondary imaging coil to the primary imaging coil in the imaging coil assembly of FIG. 6, according to some embodiments of the present invention.
Figure 9B:
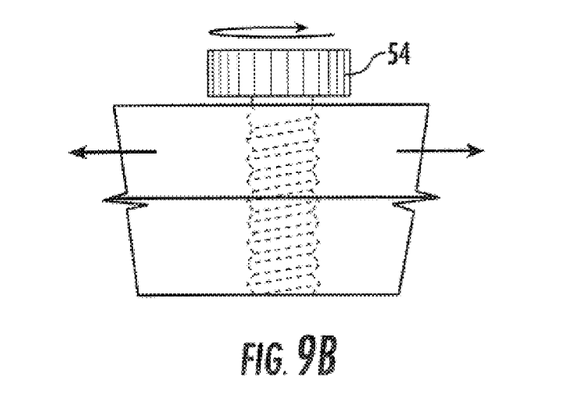
Figure 9C:
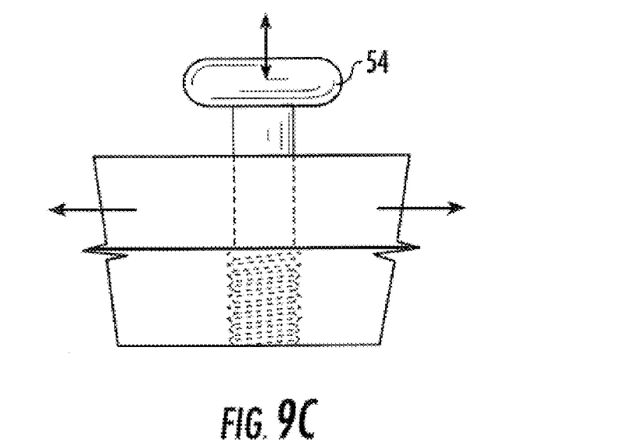

FIGS. 6-8 illustrate an MRI imaging coil assembly 16 according to is another embodiment of the present invention. The illustrated MRI imaging coil assembly 16 includes a primary external MRI imaging coil 30" and a secondary external MRI imaging coil 40"" positioned proximate to the primary MRI imaging coil 30". The secondary imaging coil 40"" can have an arcuate shape and is configured to slide telescopically along the inner periphery of the primary imaging coil 30". The secondary imaging coil 40"" can include a pair of spaced-apart slots 52 that engage respective locking members 54. Locking members 54 can be loosened to permit the secondary imaging coil 40"" to move along the axial direction $A_1$ and can be tightened to secure the secondary imaging coil 40"" in a desired location. FIGS. 9A-9C illustrate exemplary types of locking members 54 (e.g., clamping devices FIG. 9A, threaded devices FIG. 9B, and pull up devices FIG. 9C) for securing the secondary imaging coil 40"" to the primary imaging coil 30".

The illustrated primary imaging coil 30" has an open-face, substantially U-shaped configuration with spaced-apart leg portions 30a, 30b having free ends. The primary imaging coil 30" is configured to be secured to the head support assembly 14 via head engagement rods 22 that are adjustably associated with each respective arm 18, 20, as illustrated in FIG. 7. Each head engagement rod 22 is inserted through a grommet 24 that is configured to cooperate with a respective opposing slot 32 in the primary imaging coil 30". The grommets 24 allow the primary imaging coil 30" to move along an axial direction $A_1$ relative to the head of a patient secured to the head support assembly 14.

FIG. 8 illustrates directional movement of the primary and secondary imaging coils 30" and 40"". Vertical movement of the primary and secondary imaging coils 30" and 40"" (i.e., movement along direction $D_2$) can be achieved via the insertion and removal of shims (not shown) or via other mechanisms well known in the art.

FIG. 10 illustrates an MRI imaging coil assembly 16 according to another embodiment of the present invention. The illustrated MRI imaging coil assembly 16 includes a primary external MRI imaging coil 30' and a secondary external MRI imaging coil 140 secured to a targeting frame 100 and positioned proximate to the primary MRI imaging coil 30'. The secondary imaging coil 140' can have, but is not limited to, an oval shape. This secondary imaging coil 140 can be described as a local imaging coil focused to the frame 100, burr hole or is other "local" view, rather that the entire head H. In some embodiments, the secondary imaging coil 140' is attached directly to the targeting frame 100 (e.g., via threaded fasteners, etc.). The secondary imaging coil 140' may have various shapes and sizes.

Figure 11A:
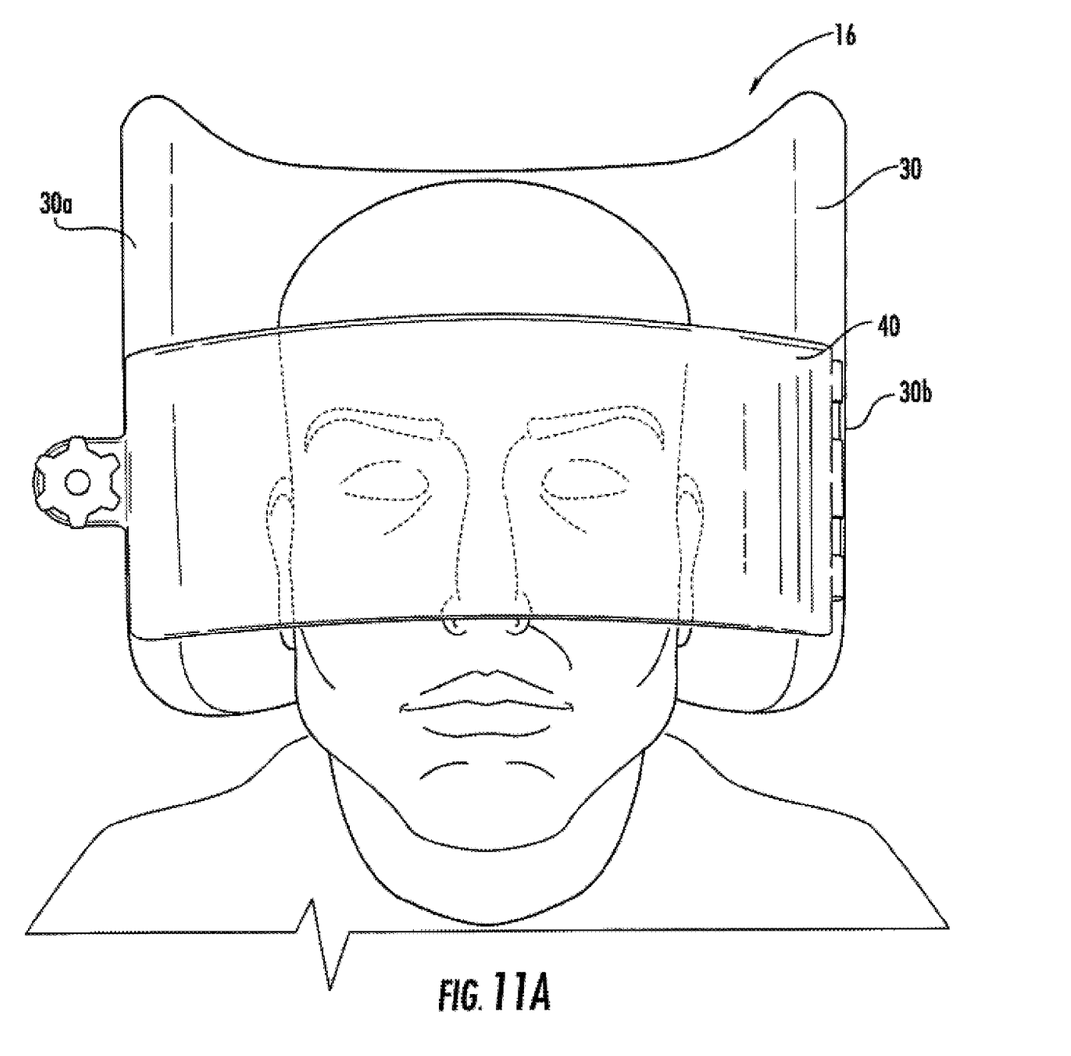
FIGS. 11A-11B illustrate an MRI imaging coil assembly, according to some embodiments of the present invention.
Figure 11B:
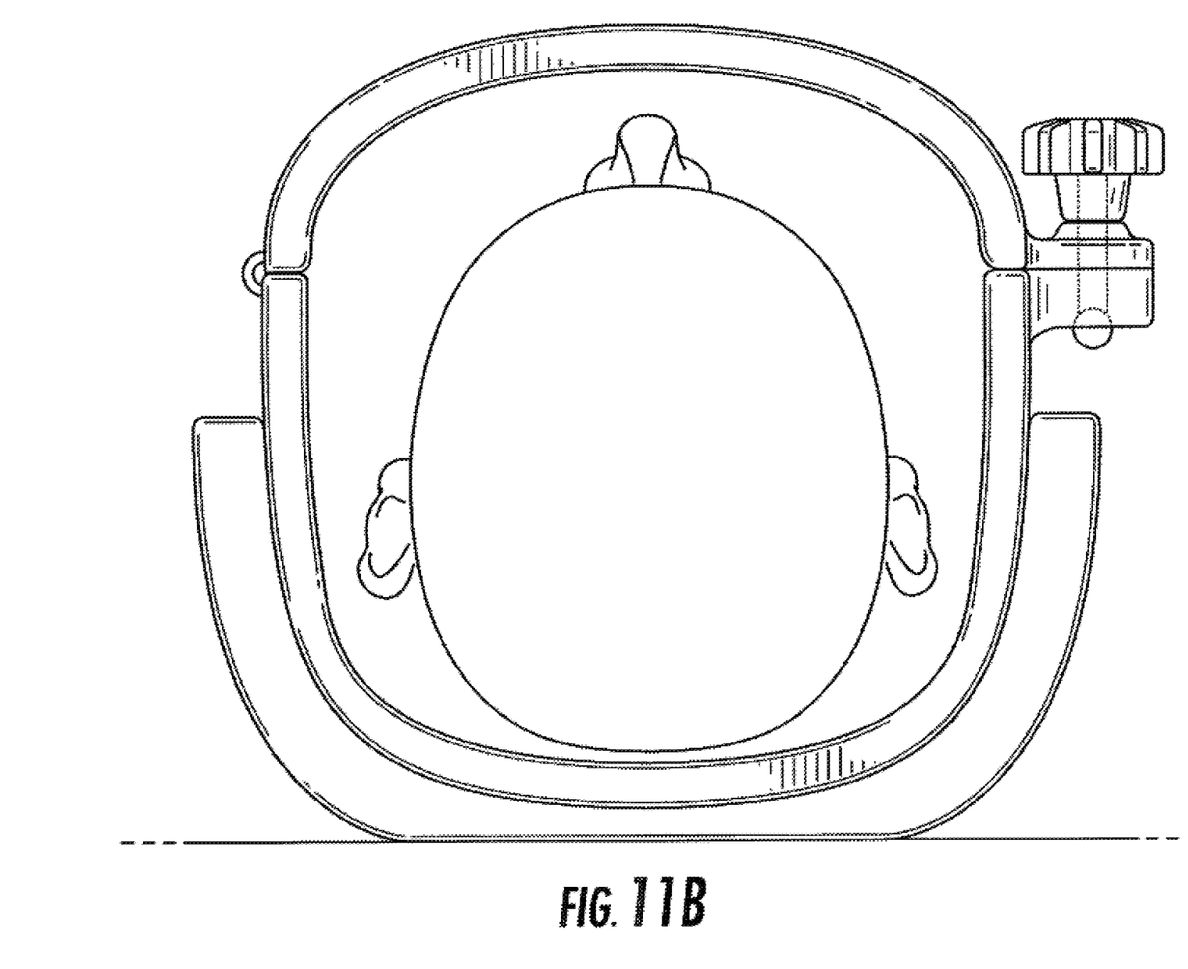

Referring to FIGS. 11A-11B, an MRI imaging coil assembly 16, according to other embodiments of the present invention, is illustrated. The MRI imaging coil assembly 16 includes a primary external imaging coil 30 and a secondary external imaging coil 40 positioned proximate to the primary imaging coil 30. As described above, the primary imaging coil 30 has a plurality of spaced-apart RF coils, along with circuitry for controlling RF excitation of the RF coils. The secondary imaging coil 40 has at least one RF coil, and is secured to the primary imaging coil 30 so as to overlie only a portion of the face of a patient. For example, in some embodiments, the secondary imaging coil 40 can be about three inches (3") wide so as to cover from just below the nose of a patient to the patient's eyebrow. However, embodiments of the present invention are not limited to a particular width of the secondary imaging coil 40. The secondary imaging coil 40 can have various widths, as well as various shapes and configurations. Moreover, the secondary imaging coil 40 need not be arcuate. The primary and secondary imaging coils 30, 40 cooperate to provide MRI signals to an MRI scanner.

The illustrated secondary imaging coil 40 is arcuate in shape and is secured to the free ends of the leg portions 30a, 30b of the primary imaging coil. In some embodiments, the secondary imaging coil 40 may be hingedly attached to one of the leg portions 30a, 30b of the primary imaging coil 30. In some embodiments, the secondary imaging coil 40 may be removably secured to the primary imaging coil 30. In some embodiments, the secondary imaging coil 40 may be movably secured to the leg portions 30a, 30b of the primary imaging coil 30, and configured to slide along a longitudinal direction defined by the primary imaging coil. In yet further embodiments, the secondary imaging coil may be integral with the primary imaging coil 30. In other words, the primary and secondary imaging coils 30, 40 can be a unitary apparatus.

All of the components associated with the various head coil assemblies described above (i.e., the head support assemblies, the head engagement rods, the various primary and secondary imaging coils) are formed from or include MRI-compatible material. Exemplary MRI-compatible materials include, but are not limited to, various polymeric materials (e.g., plastics), carbon fiber materials, glass-filled epoxies, and metals such as nickel-titanium alloys (e.g., Nitinol). As known to those skilled in the art of MRI, Nitinol is non-ferromagnetic with a lower magnetic susceptibility than conventional stainless steel.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An MRI imaging coil assembly, comprising:
   a primary external MRI imaging coil having an open-face, substantially U-shaped configuration with spaced-apart leg portions that is adapted to surround at least a portion of a patient, and comprising plurality of spaced-apart RF coils; and
   a secondary external MRI imaging coil comprising a panel with opposite sides and opposite ends and including at least one RF coil, wherein each panel end is secured to an end of a respective one of the leg portions of the primary MRI imaging coil such that the entire secondary MRI imaging coil extends from one primary imaging coil leg portion to the other leg portion;
   wherein the primary and secondary imaging coils cooperate to provide MRI signals to an MRI scanner.

2. The MRI imaging coil assembly of claim 1, wherein an image produced by the MRI imaging coil assembly has no greater than one-hundred percent (100%) difference in signal-to-noise ratio (SNR) across a volume thereof.

3. The MRI imaging coil assembly of claim 1, wherein the secondary MRI imaging coil panel has a width between opposite sides of about three inches.

4. The MRI imaging coil assembly of claim 1, wherein the ends of the secondary MRI imaging coil panel are each secured to a respective one of the leg portion ends of the primary MRI imaging coil in only a single static location.

5. The MRI imaging coil assembly of claim 1, wherein the secondary MRI imaging coil panel has a substantially U-shaped configuration and extends above and over the primary MRI imaging coil.

6. The MRI imaging coil assembly of claim 1, wherein the secondary MRI imaging coil panel has an arcuate configuration.

7. The MRI imaging coil assembly of claim 1, wherein the secondary MRI imaging coil panel has a substantially rectangular configuration.

8. The MRI head coil assembly of claim 1, wherein the ends of the secondary imaging coil panel are each secured to a respective one of the leg portion ends of the primary imaging coil in only a single static location.

9. The MRI head coil assembly of claim 1, wherein the secondary imaging coil panel includes substantially parallel opposite side portions and substantially parallel opposite ends.

10. The MRI head coil assembly of claim 1, wherein the secondary imaging coil panel has a substantially rectangular configuration when viewed from the top.

11. An MRI-guided interventional system, comprising:
    a patient support surface;
    a head support assembly attached to the patient support surface for immobilizing the head of a patient during an MRI-guided procedure;
    a targeting frame configured to be secured to the skull of a patient, wherein the frame includes a cooperating targeting cannula that is configured to guide placement of an interventional device in vivo; and
    an MRI imaging coil assembly, comprising:
       a primary external MRI imaging coil positioned proximate to the head support assembly and configured to surround at least a portion of the head of the patient, wherein the primary Mm imaging coil has an open-face, elongated substantially U-shaped configuration with spaced-apart leg portions, and a plurality of spaced-apart RF coils; and
       a secondary external MRI imaging coil comprising a panel with opposite sides and opposite ends and including at least one RF coil, wherein each panel end is secured to an end of a respective one of the leg portions of the primary MRI imaging coil such that the entire secondary MRI imaging coil extends from one primary imaging coil leg portion to the other leg portion;
    wherein the primary and secondary imaging coils cooperate to provide MRI signals to an MRI scanner.

12. The MRI-guided interventional system of claim 11, wherein an image produced by the MRI imaging coil assembly has no greater than one-hundred percent (100%) difference in signal-to-noise ratio (SNR) across a volume thereof.

13. The MRI-guided interventional system of claim 11, wherein the secondary MRI imaging coil panel has a width between opposite sides of about three inches.

14. The MRI-guided interventional system of claim 11, wherein the ends of the secondary MRI imaging coil panel are secured to the leg portion ends of the primary MRI imaging coil.

15. The MRI-guided interventional system of claim 11, wherein the secondary MRI imaging coil panel has a substantially U-shaped configuration and extends above and over the primary MRI imaging coil.

16. The MRI-guided interventional system of claim 11, wherein the secondary MRI imaging coil panel has a substantially rectangular configuration.

17. The MRI-guided interventional system of claim 11, wherein the secondary MRI imaging coil is focused to an interventional device.

18. The MRI-guided interventional system of claim 11, wherein the head support assembly comprises:
    a pair of elongated arms extending outwardly from the patient support surface in adjacent, spaced-apart relationship; and
    a pair of head engagement rods, wherein each rod is adjustably associated with a respective arm, and wherein the rods are configured to engage a patient's head positioned between the arms.

19. The MRI-guided interventional system of claim 18, wherein the primary MRI imaging coil is positioned between the head support assembly arms such that the leg portion ends extend upwardly.

20. The MRI-guided interventional system of claim 11, wherein the primary MRI imaging coil is movable relative to the head support assembly in one or more directions.

21. An MRI-guided interventional system, comprising:
    a patient support surface;
    a head support assembly attached to the patient support surface for immobilizing the head of a patient during an MRI-guided procedure;
    a targeting frame configured to be secured to the skull a patient, wherein the frame includes a cooperating targeting cannula that is configured to guide placement of an interventional device in vivo; and an MRI imaging coil assembly, comprising:

a primary external MRI imaging coil positioned proximate to the head support assembly and configured to surround at least a portion of the head of a patient, wherein the primary MRI imaging coil has a plurality of spaced-apart RF coils; and a pair of secondary external MRI imaging coils movably positioned proximate to the primary MRI imaging coil, each secondary MRI imaging coil having at least one RF coil.

22. An MRI coil assembly, comprising:

a primary external imaging coil having an open-face, elongated substantially U-shaped configuration with spaced-apart leg portions that is adapted to surround at least a portion of a patient, and comprising plurality of spaced-apart RF coils; and a secondary external imaging coil comprising an arcuate panel having a substantially U-shaped configuration, wherein the arcuate panel includes substantially parallel opposite sides and substantially parallel opposite ends, wherein the arcuate panel includes at least one RF coil, and wherein each arcuate panel end is secured to an end of a respective one of the leg portions of the primary imaging coil such that the entire secondary imaging coil extends upwardly and over the primary imaging coil from one primary imaging coil leg portion to the other leg portion;

wherein the primary and secondary imaging coils cooperate to provide MRI signals to an MRI scanner.

23. An MRI head coil assembly, comprising:

a primary external imaging coil having an open-face, elongated substantially U-shaped configuration with spaced-apart leg portions that is adapted to surround at least a portion of a head of a patient, and comprising a plurality of spaced-apart RF coils; and a secondary external imaging coil comprising an arcuate panel having opposite ends, opposite side portions, and a substantially U-shaped configuration, wherein the arcuate panel includes at least one RF coil, wherein each arcuate panel end is secured to an end of a respective one of the leg portions of the primary imaging coil such that the entire secondary imaging coil extends upwardly and over the primary imaging coil from one primary imaging coil leg portion to the other leg portion so as to overlie the head of a patient positioned within the primary external imaging coil, and wherein one side portion of the panel terminates proximate the lower portion of a nose of the patient and wherein the opposite side portion terminates proximate the forehead of the patient;

wherein the primary and secondary imaging coils cooperate to provide MRI signals to an MRI scanner.

24. The MRI head coil assembly of claim 23, wherein an image produced by the MRI head coil assembly has no greater than one-hundred percent (100%) difference in signal-to-noise ratio (SNR) across a volume thereof.

25. The MRI head coil assembly of claim 23, wherein a width between the opposite side portions is about three inches.

* * * * *

UNITED STATES PATENT AND TRADEMARK OFFICE
CERTIFICATE OF CORRECTION

PATENT NO. : 7,602,190 B2  
APPLICATION NO. : 12/237102  
DATED : October 13, 2009  
INVENTOR(S) : Piferi et al.

Page 1 of 1

It is certified that error appears in the above-identified patent and that said Letters Patent is hereby corrected as shown below:

On the Title Page  
Item (60) Related U.S. Application Data: Please add -- Utility Application No. 12/134,412 filed June 6, 2008 --

In the Claims  
Column 10, Claim 11, Line 9: Please correct "Mm" to read -- MRI --.

Signed and Sealed this  
Thirteenth Day of December, 2011

David J. Kappos  
*Director of the United States Patent and Trademark Office*